United States Patent
Kim et al.

(10) Patent No.: US 11,029,504 B2
(45) Date of Patent: Jun. 8, 2021

(54) WINDOW APPARATUS FOR OBTAINING MICROSCOPIC IMAGE OF IN VIVO BREAST TISSUE AND METHOD FOR OBTAINING IMAGE USING SAME

(71) Applicants: MEDICINAL BIOCONVERGENCE RESEARCH CENTER, Gyeonggi-do (KR); KOREA ADVANCED INSTITUTE OF SCIENCE AND TECHNOLOGY, Daejeon (KR)

(72) Inventors: Pil Han Kim, Daejeon (KR); Yeseul Kim, Daejeon (KR); Inwon Park, Daejeon (KR); Sunghoon Kim, Seoul (KR)

(73) Assignees: MEDICINAL BIOCONVERGENCE RESEARCH CENTER, Gyeonggi-Do (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 587 days.

(21) Appl. No.: 15/756,394

(22) PCT Filed: Aug. 31, 2016

(86) PCT No.: PCT/KR2016/009719
§ 371 (c)(1),
(2) Date: Feb. 28, 2018

(87) PCT Pub. No.: WO2017/039315
PCT Pub. Date: Mar. 9, 2017

(65) Prior Publication Data
US 2018/0235476 A1 Aug. 23, 2018

(30) Foreign Application Priority Data
Aug. 31, 2015 (KR) .................. KR10-2015-0123212

(51) Int. Cl.
*G02B 21/00* (2006.01)
*A61B 5/00* (2006.01)
(Continued)

(52) U.S. Cl.
CPC .......... *G02B 21/0028* (2013.01); *A61B 90/25* (2016.02); *G02B 21/0032* (2013.01);
(Continued)

(58) Field of Classification Search
CPC ................ G02B 21/0028; G02B 21/34; G02B 21/0032; G02B 21/0076; G02B 21/02;
(Continued)

(56) References Cited

U.S. PATENT DOCUMENTS

| 2006/0275896 A1* | 12/2006 | Anderson | C12M 23/22 435/303.1 |
| 2011/0043618 A1* | 2/2011 | Salisbury | G02B 21/32 348/79 |
| 2015/0346476 A1* | 12/2015 | Quarre | G02B 21/24 359/391 |

FOREIGN PATENT DOCUMENTS

| JP | 09-035317 A | 2/1997 |
| JP | 2002-537573 A | 11/2002 |

(Continued)

OTHER PUBLICATIONS

First Examiner's Report in corresponding Chinese Application No. 201680062598.4 dated May 11, 2020.
(Continued)

*Primary Examiner* — Geroge G King
(74) *Attorney, Agent, or Firm* — Leason Ellis LLP (57) ABSTRACT

Disclosed are a window apparatus for obtaining a microscopic image of in vivo breast tissue and a method for using the window apparatus to obtain cell-level and molecular-level microscopic images of in vivo breast tissue while
(Continued)

maintaining the biological environment of the in vivo breast tissue. In one embodiment, a window apparatus comprises a first chamber having a ring structure with an open window on the center, and a cover glass disposed on the upper part and breast tissue placed on the lower part; a second chamber having an opening window on the center coupled to the first chamber to support the breast tissue; and a chamber holder for fixing the first and second chambers having a tilting mount placing unit with the tilting mount placed to have the cover glass and an object lens of a confocal microscope system stay parallel to each other.

**7 Claims, 7 Drawing Sheets
(5 of 7 Drawing Sheet(s) Filed in Color)**

(51) Int. Cl.
   *A61B 90/25* (2016.01)
   *G02B 21/34* (2006.01)
   *G02B 21/26* (2006.01)

(52) U.S. Cl.
   CPC ............. *G02B 21/34* (2013.01); *A61B 5/00* (2013.01); *A61B 5/0091* (2013.01); *A61B 2503/40* (2013.01); *A61B 2562/0233* (2013.01); *G02B 21/0076* (2013.01); *G02B 21/26* (2013.01)

(58) Field of Classification Search
   CPC ........... G02B 21/26; A61B 5/00; A61B 90/25; A61B 5/0091; A61B 2503/40; A61B 2562/0233
   USPC .................................................. 359/391, 398
   See application file for complete search history.

(56) References Cited

FOREIGN PATENT DOCUMENTS

| | | |
|---|---|---|
| JP | 2007-536969 A | 12/2007 |
| KR | 10-1990-0701215 A | 12/1990 |
| KR | 10-2010-0063840 A | 6/2010 |
| WO | WO 2006/124672 A2 | 11/2006 |

OTHER PUBLICATIONS

International Search Report and Written Opinion in corresponding PCT Application No. PCT/KR2016/009719, dated Dec. 6, 2016.

\* cited by examiner

FIG. 8 ial Patent Application
WINDOW APPARATUS FOR OBTAINING MICROSCOPIC IMAGE OF IN VIVO BREAST TISSUE AND METHOD FOR OBTAINING IMAGE USING SAME This is a continuation of International Patent Application No. PCT/KR2016/009719, filed Aug. 31, 2016, which claims priority from Korean Patent Application No. 10-2015-0123212, filed on Aug. 31, 2015, which are hereby incorporated by reference for all purposes as if fully set forth herein.

TECHNICAL FIELD

The present disclosure relates to a window apparatus for obtaining a microscopic image of an in vivo breast tissue and a method for obtaining image using the same.

BACKGROUND ART

A confocal laser scanning microscope using fluorescent signals is used to observe cellular-level and molecular-level phenomenon.

Evaporation of moisture and inflammation may be generated on the breast tissues existing under the skin, unlike other tissues, due to cutting of the skin for taking images of the breast tissues, so there is a limit in a repetitive and long-term imaging technology.

Due to this limit, most molecular biological studies are performed in the process of extracting, fixing, and then observing tissues.

According to this method, it is difficult to observe changes in movement or shape of cells in living animal and it is difficult to conduct a study by observing lactiferous ducts, which are a characteristic of breast tissues, and vascular tissues around the lactiferous ducts.

It is an important subject in a microscopic image study of breast tissues in vivo to find out for a long period of time cellular-level and molecular-level structures and interactions while maintaining the physiological environment of living animals.

Accordingly, there is a need for an apparatus that can repeatedly obtain images of the same cell and tissue for a long time while observing a molecular biological mechanism that occurs in a lactiferous duct and a blood vessel in a breast tissue of a living creature.

DETAILED DESCRIPTION OF THE INVENTION

Technical Problem

In order to solve the problems in the related art described above, the present disclosure provides a window apparatus for obtaining microscopic image in vivo of a breast tissue, the apparatus can obtain real-time cellular-level and molecular-level microscopic images of a lactiferous duct and a blood vessel of a breast tissue stably and for a long period of time without extracting the breast tissue while maintaining an in vivo environment, and a method of obtaining an image using the apparatus.

Technical Solution

According to an embodiment, there is provided a window apparatus for obtaining an in vivo microscopic image of a breast tissue, the window apparatus comprising: a first chamber configured to have a ring-shaped structure with an open window at the center of the first chamber wherein a cover glass is placed on the upper part of the first chamber and a breast tissue is placed on the lower part of the first chamber; a second chamber configured to have an open window at the center of the second chamber wherein the second chamber is combined with the first chamber to support the breast tissue; and a chamber holder configured to fix the first chamber and the second chamber and have a tilting mount seat where a tilting mount is placed to maintain the cover glass and an objective lens of a confocal microscope system in parallel with each other.

According to an embodiment, there is provided a window apparatus for obtaining an in vivo microscopic image of a breast tissue, the window apparatus consisting of: a first chamber configured to have a ring-shaped structure with an open window at the center of the first chamber wherein a cover glass is placed on the upper part of the first chamber and a breast tissue is placed on the lower part of the first chamber; a second chamber configured to have an open window at the center of the second chamber wherein the second chamber is combined with the first chamber to support the breast tissue; and a chamber holder configured to fix the first chamber and the second chamber and have a tilting mount seat where a tilting mount is placed to maintain the cover glass and an objective lens of a confocal microscope system in parallel with each other.

According to an embodiment, there is provided a window apparatus for obtaining an in vivo microscopic image of a breast tissue, the window apparatus essentially consisting of: a first chamber configured to have a ring-shaped structure with an open window at the center of the first chamber wherein a cover glass is placed on the upper part of the first chamber and a breast tissue is placed on the lower part of the first chamber; a second chamber configured to have an open window at the center of the second chamber wherein the second chamber is combined with the first chamber to support the breast tissue; and a chamber holder configured to fix the first chamber and the second chamber and have a tilting mount seat where a tilting mount is placed to maintain the cover glass and an objective lens of a confocal microscope system in parallel with each other.

A plurality of holes that communicate with each other may be formed along the outer circumference surface of the first chamber and the outer side of the second chamber.

The first chamber and the second chamber may be combined with each other by one or more bolts or threads.

A first protrusion and a second protrusion that are stepped on sides facing each other may be formed on a side of the chamber holder, and the first chamber and the second chamber may be fixed between the first protrusion and the second protrusion.

A first chamber seat where the first chamber is placed may be formed on the first protrusion and the second protrusion.

The first chamber may be larger in outer diameter than the second chamber, the outer diameter of the first chamber may correspond to the length of first facing sides at the upper portion of the first chamber seat, and the first chamber may be tightly fitted on the first facing sides.

The outer diameter of the second chamber may correspond to the length between second facing sides at the lower part of the first chamber seat.

According to another aspect, there is provided a method for obtaining an image using a confocal microscope system and a window apparatus wherein the window apparatus comprises a first chamber, a second chamber, and a chamber holder which is configured to fix the first chamber and the second chamber combined with each other and have a tilting mount seat, the method comprising: adjusting the angle of the window apparatus by using a tilting mount placed on the tilting mount seat of the window apparatus; radiating laser beams having a plurality of wavelengths to a breast tissue through an open window of the first chamber and the second chamber, wherein a cover glass is placed on the upper part of the first chamber and a breast tissue is placed between the first chamber and the second chamber; and detecting a fluorescent signal excited in the breast tissue, wherein the cover glass and an objective lens of the confocal microscope system are maintained in parallel with each other during a process of obtaining the image by adjusting the angle of the window apparatus using the tilting mount.

According to another aspect, there is provided a method for obtaining an image using a confocal microscope system and a window apparatus wherein the window apparatus comprises a first chamber, a second chamber, and a chamber holder which is configured to fix the first chamber and the second chamber combined with each other and have a tilting mount seat, the method consisting of: adjusting the angle of the window apparatus by using a tilting mount placed on the tilting mount seat of the window apparatus; radiating laser beams having a plurality of wavelengths to a breast tissue through an open window of the first chamber and the second chamber, wherein a cover glass is placed on the upper part of the first chamber and a breast tissue is placed between the first chamber and the second chamber; and detecting a fluorescent signal excited in the breast tissue, wherein the cover glass and an objective lens of the confocal microscope system are maintained in parallel with each other during a process of obtaining the image by adjusting the angle of the window apparatus using the tilting mount.

According to another aspect, there is provided a method for obtaining an image using a confocal microscope system and a window apparatus wherein the window apparatus comprises a first chamber, a second chamber, and a chamber holder which is configured to fix the first chamber and the second chamber combined with each other and have a tilting mount seat, the method essentially consisting of: adjusting the angle of the window apparatus by using a tilting mount placed on the tilting mount seat of the window apparatus; radiating laser beams having a plurality of wavelengths to a breast tissue through an open window of the first chamber and the second chamber, wherein a cover glass is placed on the upper part of the first chamber and a breast tissue is placed between the first chamber and the second chamber; and detecting a fluorescent signal excited in the breast tissue, wherein the cover glass and an objective lens of the confocal microscope system are maintained in parallel with each other during a process of obtaining the image by adjusting the angle of the window apparatus using the tilting mount.

The term 'comprising' used herein have the same meaning as terms 'including' or 'characterized by', not excluding additional non-stated elements, components, or steps in an apparatus or a method. The term 'consisting of' excludes additional elements, steps, or components not specifically stated. The term 'essentially consisting of' means comprising elements, components, or steps that do not actually influence basic characteristics in addition to stated elements, components, or steps in an apparatus or a method.

Advantageous Effects

According to embodiments of the present invention which use two chambers configured to have an open window and place a breast tissue therebetween, and a chamber holder configured to fix the two chambers and have a tilting mount seat where a tilting mount is placed, there is an advantage of stably obtaining images since it is possible to maintain the open window and an objective lens of the microscope in parallel while a living animal is placed on an objective area of a microscope.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODE FOR CARRYING OUT THE INVENTION

The present disclosure may be modified in various ways and implemented by various exemplary embodiments, so that specific exemplary embodiments are shown in the drawings and will be described in detail.

However, it is to be understood that the present disclosure is not limited to the specific exemplary embodiments, but includes all modifications, equivalents, and substitutions included in the spirit and the scope of the present disclosure. Reference numerals are assigned to reference components in the following description of drawings.

Hereinafter, exemplary embodiments will be described in detail with reference to the accompanying drawings.

Figure 1:
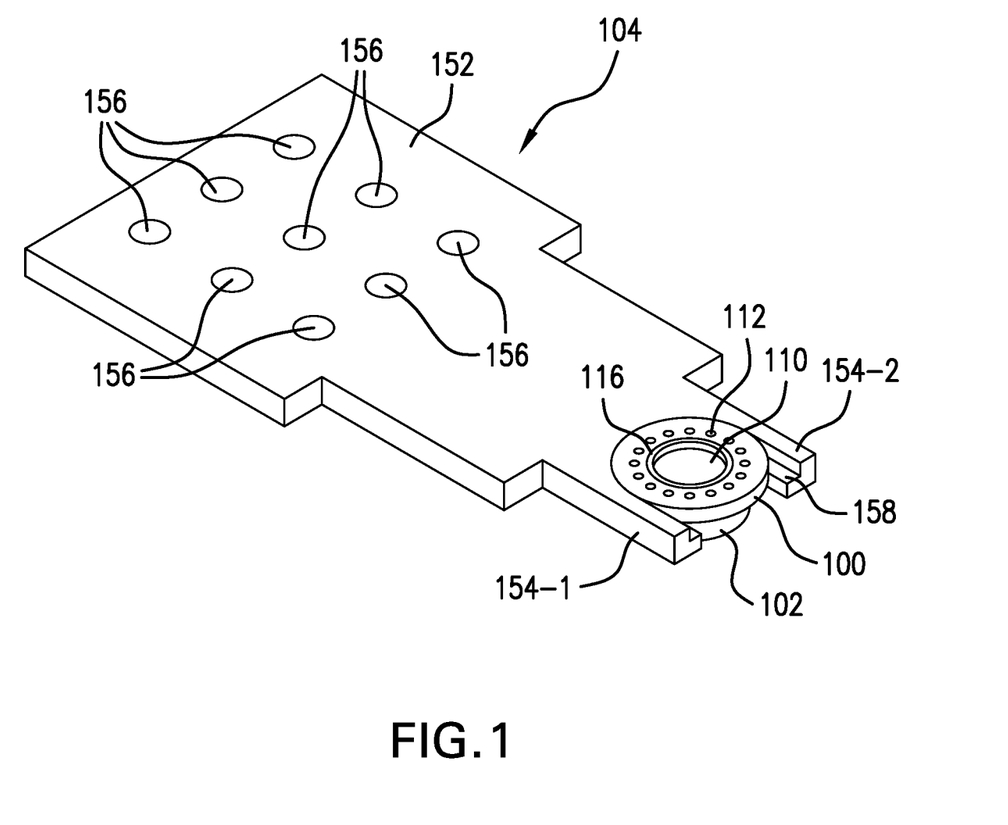
FIG. 1 is a perspective view showing a window apparatus according to an embodiment.
Figure 2:
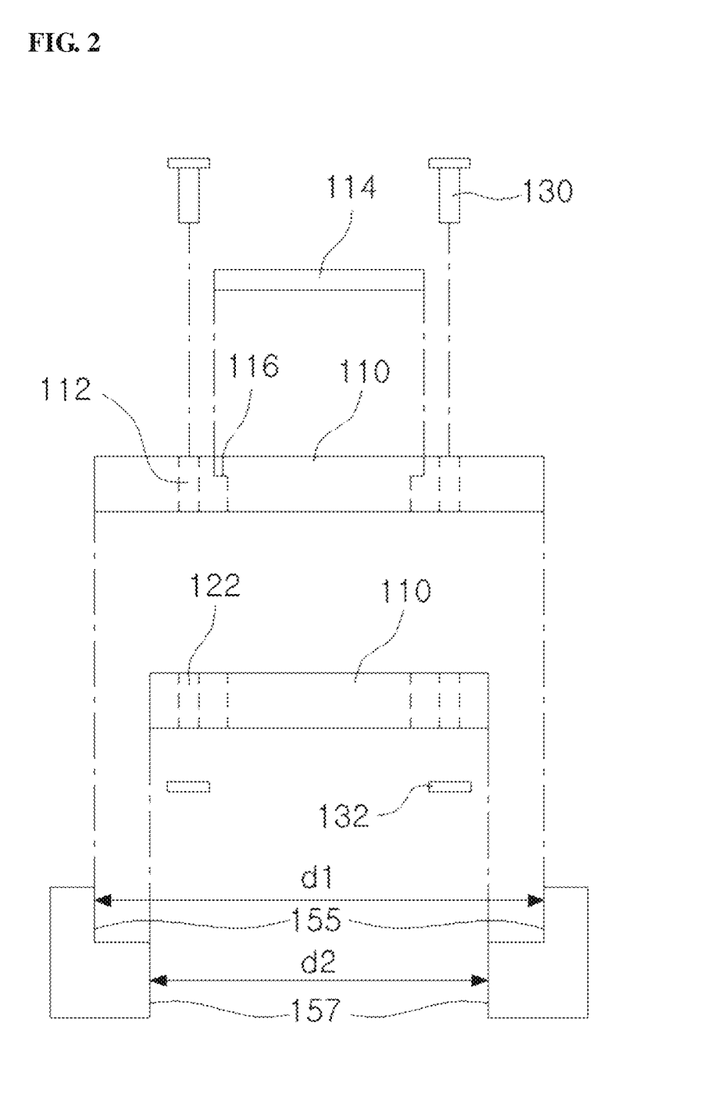
FIG. 2 is a vertical cross-sectional view of the window apparatus according to an embodiment.
Figure 3:
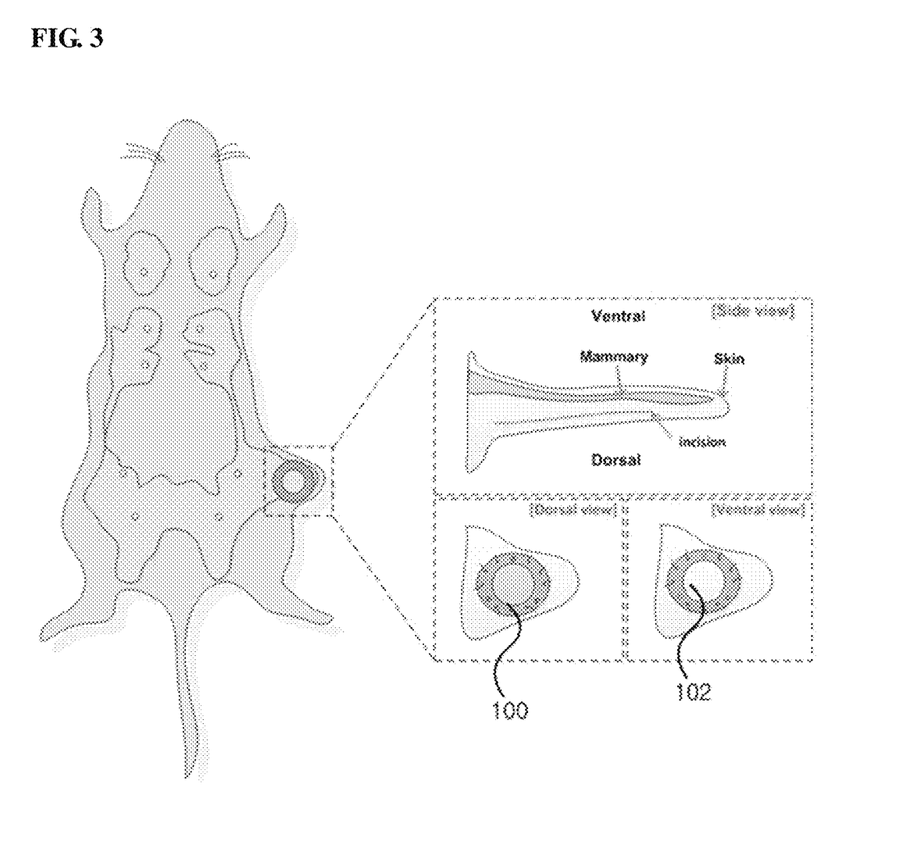
FIG. 3 is a view showing the use state of the window apparatus according to an embodiment.

FIG. 1 is a perspective view showing a window apparatus according to an embodiment, FIG. 2 is a vertical cross-sectional view of the window apparatus according to an embodiment, and FIG. 3 is a view showing the use state of the window apparatus according to an embodiment.

As shown in FIGS. 1 to 3, a window apparatus according to an embodiment may include a first chamber 100, a second chamber 102, and a chamber holder 104.

The first chamber 100 and second chamber 102 have a ring-shaped structure with an open window at the center.

The first chamber 100 is disposed close to an objective lens 140 of a confocal microscope system and has a cover glass seat 116 where a cover glass 114 is placed.

A plurality of holes 112 and 122 that can communicate with each other are formed respectively outside the first chamber 100 and the second chamber 102.

According to a preferred embodiment, in order to observe a breast tissue of an animal, as shown in FIG. 3, the skin of a breast of the animal is cut and a cut breast tissue is placed between the first chamber 100 and the second chamber 102.

The tissue placed between the first chamber 100 and the second chamber 102 is observed through the open window 110 of the first chamber 100 and the second chamber 102.

The first chamber 100 and the second chamber 102 are combined by a plurality of bolts 130, nuts 132, and threads (not shown).

According to the embodiment, a chamber holder 104 is provided to fix the first chamber 100 and the second chamber 102 and keep the cover glass 114 placed on the first chamber 100 and the objective lens 140 in parallel.

The chamber holder 104 may have a tilting mount seat 152 where a tilting mount is placed and two protrusions of a first protrusion 154-1 and a second protrusion 154-2 that extending from a side of the tilting mount seat 152.

The tilting mount seat 152 has a plurality of fastening holes 156 and the tilting mount is coupled to at least some of the fastening holes 156.

The first protrusion 154-1 and the second protrusion 154-2 extend in parallel with each other and each have a stepped portion.

Preferably, a first chamber seat 158 is formed on the sides facing each other of the first protrusion 154-1 and the second protrusion 154-2.

According to the embodiment, the first chamber 100 is larger in outer diameter than the second chamber 102.

The outer diameter of the first chamber 100 corresponds to the length d1 between first facing sides 155 of the first protrusion 154-1 and the second protrusion 154-2.

The outer diameter of the second chamber 102 corresponds to the length d2 between second facing sides 157 of the first protrusion 154-1 and the second protrusion 154-2.

Accordingly, the first chamber 100 and the second chamber 102 are tightly fitted on the first facing sides 155 and the second facing sides 157.

The first chamber 100 and the second chamber 102 fitted to each other, as described above, are fixed to the chamber holder 104 and then the angle of the window apparatus is adjusted through the tilting mount placed on the tilting mount seat 152.

The tilting mount (not shown) according to the embodiment may be a kinematic tilting mount.

When the cover glass 114 disposed on the first chamber 100 and the objective lens 140 are fixed in parallel with each other by adjusting the angle of the window apparatus through the kinematic tilting mount, it is possible to stably obtain images of a same part for a long period of time.

Figure 4:
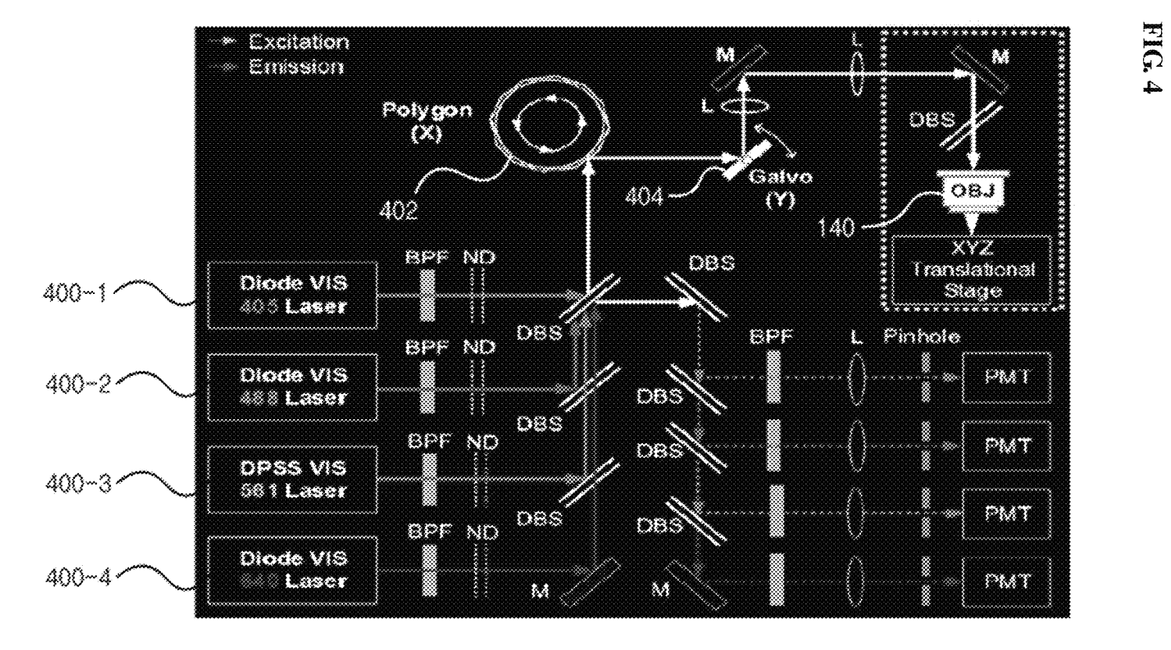
FIG. 4 is a view showing the configuration of a confocal microscope system according to an embodiment.

FIG. 4 is a view showing the configuration of a confocal microscope system according to an embodiment.

A process of obtaining an image according to the embodiment is as follows.

(1) Adjustment of Angle of Window Apparatus

The angle of the window apparatus is adjusted using the tilting mount placed on the tilting mount seat 152 of the window apparatus.

(2) Emission of Laser Beam

As in FIG. 4, laser beams having a plurality of wavelengths are radiated to a breast tissue through the open window 110 of the window apparatus.

(3) Detection of Fluorescent Signal

A fluorescent signal excited in the cancer tissue is detected through a detector.

Referring to FIG. 4, the confocal microscope system according to the embodiment includes four laser sources 400-1 to 400-4 respectively four wavelengths of 405 nm, 488 nm, 561 nm, and 640 nm within the visible light band, a polygonal rotation mirror 402, and a galvanometer mirror 404, and generates s XY raster scanning pattern, using these components.

The confocal microscope system may include a plurality of neutral density filters ND, mirrors M, and Dichroic beam splitters DBS, and beam pass filters BPF and photomultiplier tubes(PMT) for detecting a fluorescent signal excited in a breast tissue.

Images of a breast tissue were obtained from an actual animal model, using the confocal optical microscope using the window apparatus of the present disclosure.

An optical system was designed to have an observation view of 250×250 μm$^2$ at the focus when using a ×40 objective lens (LUCPlanFL, NA0.6; Olympus), and a fluorescent signal was detected and processed by photomultiplier tubes and frame grabbers (Matrox, SOLIOS) that are provided for respective wavelengths such that 2D images having cellular-level resolution and being able to be sectioned in the Z-axial direction could be obtained at a speed of 30 sheets per second.

Figure 5:
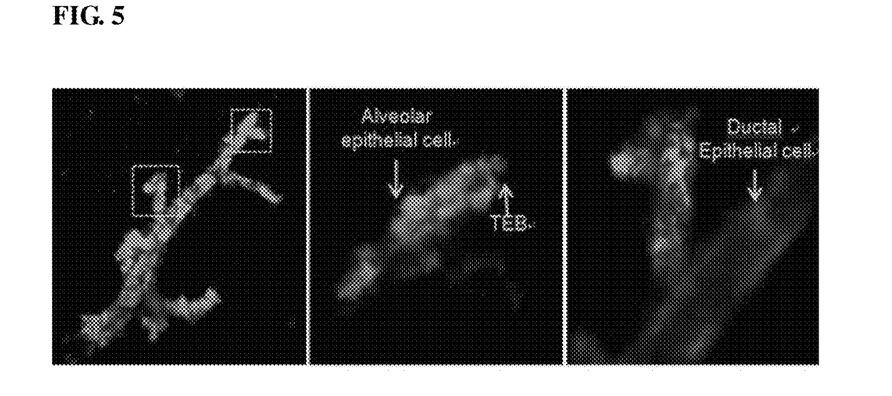
FIG. 5 shows pictures of the cells and structure of an imaged lactiferous duct of an Actin-GFP mouse, using the window apparatus and the confocal microscope system according to an embodiment.

FIG. 5 is a view showing the cells and structure of an imaged lactiferous duct of an Actin-GFP mouse, using the window apparatus and the confocal microscope system according to an embodiment.

As shown in FIG. 5, it was found that it was possible to observe an alveolar epithelial cell and a ductal epithelial cell that are lactiferous structures.

Figure 6:
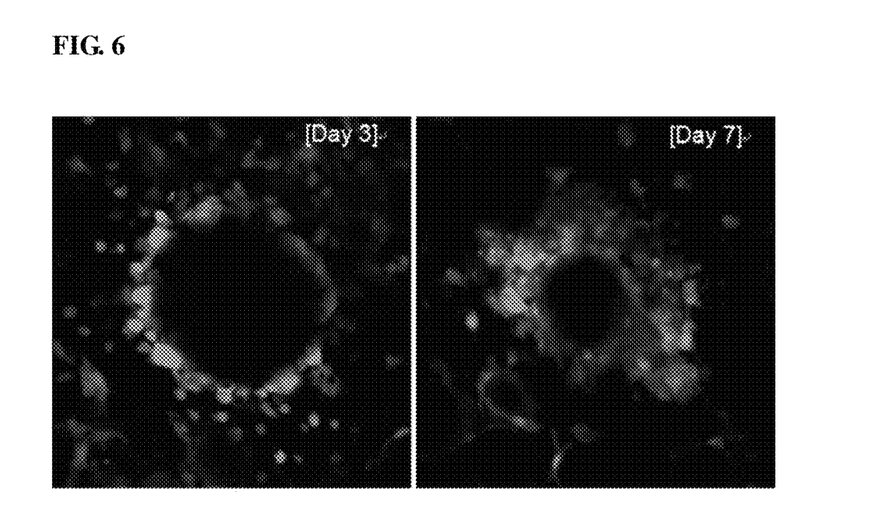
FIG. 6 shows pictures obtained by observing a lactiferous duct formation process at a cellular-level, using the window apparatus and the confocal microscope system according to an embodiment.

FIG. 6 is a view obtained by observing a lactiferous duct formation process at a cellular-level, using the window apparatus and the confocal microscope system according to an embodiment.

Figure 7:
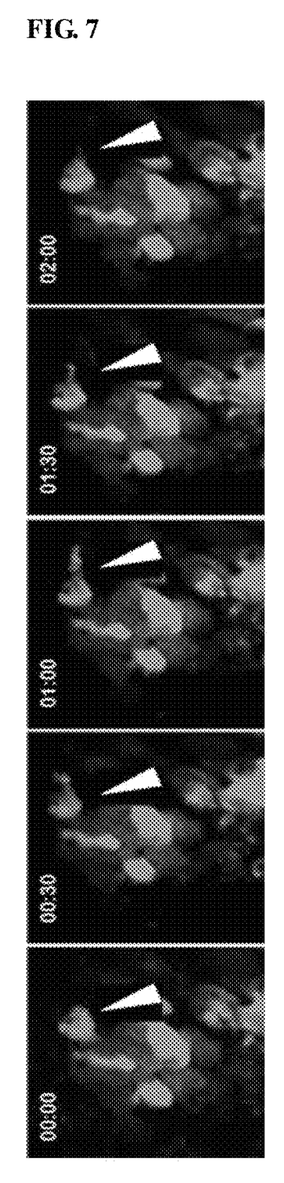
FIG. 7 shows pictures obtained by observing movement of a cell in terms of 30 minutes after implanting and culturing a breast cancer cell, MDA-MB-231-GFP Cell in a breast tissue.

FIG. 7 shows pictures obtained by observing movement of a cell at intervals of 30 minutes after implant and culture a breast cancer cell, MDA-MB-231-GFP Cell in a breast tissue.

As shown in FIGS. 6 and 7, it was possible to observe changes in shape of a cancer cell at a cellular-level by maintaining movement due to respiration and circulation of an animal, using the window apparatus according to the embodiment, with the window apparatus and the objective lens maintained in parallel.

Figure 8:
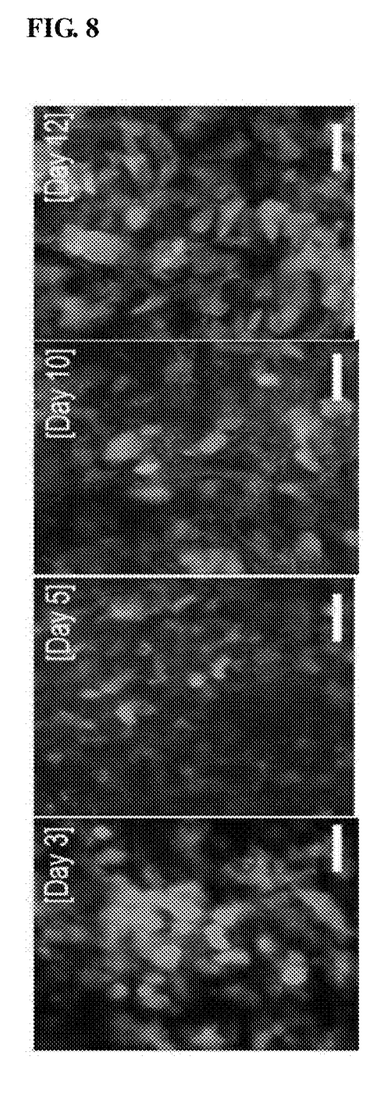
FIG. 8 shows pictures obtained by observing blood vessels formed around a cancer cell, using the window apparatus and the confocal microscope according to an embodiment.

FIG. 8 shows pictures obtained by observing blood vessels formed around a cancer cell, using the window apparatus and the confocal microscope system according to an embodiment.

Referring to FIG. 8, it was possible to find dense blood vessels that a cancer cell has formed around it for metabolism by staining an antibody CD31 with a fluorescent substance.

Hereinabove, although the present disclosure is described by specific matters such as concrete components, and the like, embodiments, and drawings, they are provided only for assisting in the entire understanding of the present disclosure. Therefore, the present disclosure is not limited to the embodiments. Various modifications and changes may be made by those skilled in the art to which the present disclosure pertains from this description. Therefore, the sprit of the present disclosure should not be limited to the above-described embodiments, and the following claims as well as all modified equally or equivalently to the claims are intended to fall within the scope and spirit of the disclosure.

The invention claimed is:

1. A window apparatus for obtaining an in vivo microscopic image of a tissue, the window apparatus comprising:
   a first chamber configured to have a ring-shaped structure with an open window at the center of the first chamber wherein a cover glass is placed on a cover glass seat configured in an upper part of the first chamber and a lower part of the first chamber is configured to hold a tissue for obtaining the in vivo microscopic image of the tissue;
   a second chamber without an associated cover glass configured to have an open window at the center of the second chamber wherein the first chamber and the second chamber are configured to combine with each other, thereby holding the tissue between the first chamber and the second chamber for obtaining the in vivo microscopic image of the tissue; and
   a chamber holder configured to fix the first chamber and the second chamber and have a tilting mount seat,
   wherein the chamber holder is configured to have a first protrusion and a second protrusion extending from a side of the tilting mount seat, and wherein the sides of said two protrusions facing each other are stepped, and the first chamber and the second chamber are fixed between the first protrusion and the second protrusion.

2. The window apparatus of claim 1, wherein a plurality of holes that communicate with each other are formed along the outer circumference surface of the first chamber and the second chamber.

3. The window apparatus of claim 2, wherein the first chamber and the second chamber are combined with each other by one or more bolts or threads.

4. The window apparatus of claim 1, wherein a first chamber seat where the first chamber is placed is formed on the first protrusion and the second protrusion.

5. The window apparatus of claim 4, wherein the outer diameter of the first chamber is larger than that of the second chamber, the outer diameter of the first chamber corresponds to a length between first facing sides at an upper part of the first chamber seat, and thereby the first chamber is tightly fitted between the first facing sides.

6. The window apparatus of claim 4, wherein the outer diameter of the second chamber corresponds to a length between second facing sides at a lower part of the first chamber seat.

7. A method for obtaining an image using a confocal microscope system and a window apparatus wherein the window apparatus comprises a first chamber, a second chamber, and a chamber holder which is configured to fix the first chamber and the second chamber combined with each other and have a tilting mount seat, the method comprising:
   adjusting the angle of the window apparatus by using a tilting mount placed on the tilting mount seat of the window apparatus;
   radiating laser beams having a plurality of wavelengths to a breast tissue through an open window of the first chamber and the second chamber, wherein a cover glass is placed on the upper part of the first chamber and a breast tissue is placed between the first chamber and the second chamber; and
   detecting a fluorescent signal excited in the breast tissue, wherein the cover glass and an objective lens of the confocal microscope system are maintained in parallel with each other during a process of obtaining the image by adjusting the angle of the window apparatus using the tilting mount and wherein the window apparatus is the window apparatus of claim 1.

* * * * *